(12) United States Patent
Kim et al.

(10) Patent No.: US 10,881,873 B2
(45) Date of Patent: Jan. 5, 2021

(54) APPARATUS FOR RELAXING SMOOTH MUSCLES OF HUMAN BODY

(71) Applicant: COLOR SEVEN CO., LTD., Seoul (KR)

(72) Inventors: Nam Gyun Kim, Jeonbuk (KR); Kyoung Jun Park, Seoul (KR)

(73) Assignee: COLOR SEVEN CO., LTD, Seoul (KR)

( * ) Notice: Subject to any disclaimer, the term of this patent is extended or adjusted under 35 U.S.C. 154(b) by 143 days.

(21) Appl. No.: 15/921,953

(22) Filed: Mar. 15, 2018

(65) Prior Publication Data

US 2018/0221680 A1 Aug. 9, 2018

Related U.S. Application Data

(62) Division of application No. 14/130,190, filed as application No. PCT/KR2012/004297 on May 31, 2012, now Pat. No. 9,950,188.

(51) Int. Cl.
*A61N 5/06* (2006.01)
*A61H 39/00* (2006.01)
*A61H 11/00* (2006.01)

(52) U.S. Cl.
CPC ......... *A61N 5/0613* (2013.01); *A61H 39/002* (2013.01); *A61N 5/0619* (2013.01);
(Continued)

(58) Field of Classification Search
CPC .. A61N 5/0613; A61N 5/0619; A61N 5/0622; A61N 5/0625; A61N 2005/0643;
(Continued)

(56) References Cited

U.S. PATENT DOCUMENTS 5,445,608 A 8/1995 Chen et al.
5,891,022 A 4/1999 Pologe
(Continued)

FOREIGN PATENT DOCUMENTS

JP 2009000545 A 1/2009
KR 100846070 B1 7/2008
KR 1020090117342 A 11/2009

OTHER PUBLICATIONS

Yanagisawa Teruyuki, et al., "Measurement of Ca ions in cells", Ebashi Setsuro Edition Societies Press, 1990, pp. 277-289.
(Continued)

*Primary Examiner* — Ahmed M Farah
(74) *Attorney, Agent, or Firm* — Dinsmore & Shohl LLP; Yongsok Choi, Esq.

(57) ABSTRACT

An apparatus includes a controller body configured to determine whether a light irradiation mode is selected and an operation is started through a user's manipulation, the controller body comprising a wireless transmission unit configured to transform an LED driving signal output according to the selected light irradiation mode into a radio signal and transmit the radio signal, and a wireless electrode probe configured to wirelessly receive the LED driving signal from the controller body by establishing wireless communication with the wireless transmission unit. The wireless electrode probe is configured to be driven by the LED driving signal received from the controller body to emit the light of a predetermined wavelength range, which increases concentration of a material for relaxing smooth muscles of a human body.

12 Claims, 10 Drawing Sheets

(52) U.S. Cl.
CPC ........ *A61H 11/00* (2013.01); *A61H 2039/005* (2013.01); *A61H 2201/0153* (2013.01); *A61H 2201/165* (2013.01); *A61H 2201/5002* (2013.01); *A61N 2005/0626* (2013.01); *A61N 2005/0645* (2013.01); *A61N 2005/0662* (2013.01)

(58) Field of Classification Search
CPC .... A61N 2005/0644; A61N 2005/0645; A61N 2005/065; A61N 2005/0651; A61N 2005/0652; A61N 2005/0664; A61N 2005/0667; A61H 2201/50; A61H 2201/5002; A61H 2201/5005; A61H 2201/5007; A61H 2201/501; A61H 2201/5012; A61H 2201/5015; A61H 2201/5097; A61H 39/00; A61H 2039/005; A61H 2039/007; A61H 2201/16; A61H 2201/165; A61H 2201/1652
USPC .................. 607/88–91, 93, 96, 100, 101
See application file for complete search history.

(56) References Cited

U.S. PATENT DOCUMENTS

| | | | |
|---|---|---|---|
| 5,972,026 | A | 10/1999 | Laufer et al. |
| 6,083,255 | A | 7/2000 | Laufer et al. |
| 6,200,333 | B1 | 3/2001 | Laufer |
| 6,273,907 | B1 | 8/2001 | Laufer |
| 6,283,988 | B1 | 9/2001 | Laufer et al. |
| 6,283,989 | B1 | 9/2001 | Laufer et al. |
| 6,299,633 | B1 | 10/2001 | Laufer |
| 6,411,852 | B1 | 6/2002 | Danek et al. |
| 6,488,673 | B1 | 12/2002 | Laufer et al. |
| 6,634,363 | B1 | 10/2003 | Laufer et al. |
| 7,027,869 | B2 | 4/2006 | Danek et al. |
| 7,264,002 | B2 | 9/2007 | Danek et al. |
| 7,273,055 | B2 | 9/2007 | Danek et al. |
| 7,425,212 | B1 | 9/2008 | Danek et al. |
| 7,542,802 | B2 | 6/2009 | Danek et al. |
| 7,556,624 | B2 | 7/2009 | Laufer et al. |
| 7,740,017 | B2 | 6/2010 | Danek et al. |
| 7,770,584 | B2 | 8/2010 | Danek et al. |
| 7,921,855 | B2 | 4/2011 | Danek et al. |
| 7,938,123 | B2 | 5/2011 | Danek et al. |
| 7,992,572 | B2 | 8/2011 | Danek et al. |
| 8,161,978 | B2 | 4/2012 | Danek et al. |
| 8,181,656 | B2 | 5/2012 | Danek et al. |
| 8,251,070 | B2 | 8/2012 | Danek et al. |
| 8,267,094 | B2 | 9/2012 | Danek et al. |
| 2002/0091379 | A1 | 7/2002 | Danek et al. |
| 2003/0159700 | A1 | 8/2003 | Laufer et al. |
| 2004/0031494 | A1 | 2/2004 | Danek et al. |
| 2004/0044384 | A1 | 3/2004 | Leber |
| 2004/0182399 | A1 | 9/2004 | Danek et al. |
| 2005/0010270 | A1 | 1/2005 | Laufer |
| 2005/0159736 | A9 | 7/2005 | Danek et al. |
| 2005/0187579 | A1 | 8/2005 | Danek et al. |
| 2005/0228463 | A1* | 10/2005 | Mac ............... A61N 5/0619 607/89 |
| 2006/0137698 | A1 | 6/2006 | Danek et al. |
| 2006/0254600 | A1 | 11/2006 | Danek et al. |
| 2006/0278243 | A1 | 12/2006 | Danek et al. |
| 2006/0278244 | A1 | 12/2006 | Danek et al. |
| 2007/0062545 | A1 | 3/2007 | Danek et al. |
| 2007/0083197 | A1 | 4/2007 | Danek et al. |
| 2007/0102011 | A1 | 5/2007 | Danek et al. |
| 2007/0106296 | A1 | 5/2007 | Laufer et al. |
| 2007/0106348 | A1 | 5/2007 | Laufer |
| 2007/0118184 | A1 | 5/2007 | Danek et al. |
| 2007/0118190 | A1 | 5/2007 | Danek et al. |
| 2007/0123958 | A1 | 5/2007 | Laufer |
| 2008/0077198 | A1* | 3/2008 | Webb ............... A61N 5/0618 607/88 |
| 2009/0112203 | A1 | 4/2009 | Danek et al. |
| 2009/0143705 | A1 | 6/2009 | Danek et al. |
| 2009/0143776 | A1 | 6/2009 | Danek et al. |
| 2009/0192508 | A1 | 7/2009 | Laufer et al. |
| 2010/0004645 | A1 | 1/2010 | Jeong |
| 2010/0185190 | A1 | 7/2010 | Danek et al. |
| 2010/0204689 | A1 | 8/2010 | Danek et al. |
| 2011/0031889 | A1 | 2/2011 | Shim |
| 2011/0079230 | A1 | 4/2011 | Danek et al. |
| 2012/0016174 | A1* | 1/2012 | De Taboada ........ A61N 5/0613 600/2 |
| 2012/0143236 | A1 | 6/2012 | Muzhikov |
| 2014/0324138 | A1* | 10/2014 | Wentz ............ A61N 5/0622 607/92 |
| 2016/0129281 | A1 | 5/2016 | Kim |
| 2018/0154167 | A1* | 6/2018 | Kim ............... G06Q 20/127 |
| 2019/0335551 | A1* | 10/2019 | Williams ........... H05B 47/105 |

OTHER PUBLICATIONS

T.I. Karu, "Biological action of low-intensity visible monochromatic light and some of its medical applications", International Congress on Laser in Medicine and Surgery, Jun. 26, 1985.

T.I. Karu, et al., "Effect of Irradation with Monochromatic Visible Light on cAMP Content in Chinese Hamster Fibroblasts.", IL NUOVO CIMENTO, Oct. 1987, pp. 1245-1250.

Sergei Pankratov, "Meridians conduct light", Raum and Zeit, Germany, 1991.

\* cited by examiner

APPARATUS FOR RELAXING SMOOTH MUSCLES OF HUMAN BODY

CROSS-REFERENCE TO RELATED APPLICATIONS

This application is a divisional application of U.S. application Ser. No. 14/130,190 filed on Dec. 30, 2013, which is the national phase application of PCT/KR2012/004297 filed on May 31, 2012, the entire contents of which are incorporated herein by reference.

BACKGROUND

1. Field of the Invention

The present invention relates to an apparatus for relaxing smooth muscles of a human body, and more particularly, to an apparatus for relaxing smooth muscles of a human body, which is capable of inducing relaxation of smooth muscles of a human body using an electrode probe that irradiates light having a predetermined wavelength range.

2. Discussion of Related Art

A human body has three types of muscles: skeletal muscles, smooth muscles, and cardiac muscles. Among these muscles, the skeletal muscles can be moved on a human's own will under control of motor nerves. The skeletal muscles may be intentionally contracted and relaxed through a human's efforts, e.g., exercise, massage, or rest. In contrast, the cardiac muscles and the smooth muscles are under control of autonomic nerves and cannot be moved on a human's own will.

The smooth muscles and the cardiac muscles are not easily contracted and relaxed through a human's efforts. In particular, although most internal organs, such as blood vessels and lymphatic vessels, consist of smooth muscles, a human cannot supply oxygen and nutrients to these internal organs while intentionally contracting and relaxing them. The internal organs may be supplied oxygen or nutrients by inducing blood circulation by exercising all of the internal organs through hypogastric breathing, running, or the like. However, when some of the smooth muscles need to contract and relax, they are very difficult to contract and relax through such exercises. As an example of relaxation of smooth muscles, one may feel his/her body comfort and relaxed when he/she is quietly and idly laying in warm late spring or summer sunshine.

As another example, a drug may be used to relax smooth muscles so as to increase erectility. The key principle to increasing erectility is to relax the smooth muscles of a cavernous body to a maximum level so that the cavernous body can absorb a sufficient amount of blood. It has been known that the relaxation of the smooth muscles of the cavernous body is closely related to an increase in the concentration of cyclic adenosine monophosphate (cAMP) or cyclic guanylate monophosphate (cGMP) in cells. Drugs, such as Viagra, which have been placed on the market, work based on this principle.

In particular, "Measurement of Ca ions in cells" written by Teruyuki Yanagisawa, etc. in Japan ("Progress in Blood Vessel Research", Academic Publishing Company, Tokyo, 1990, pp. 277-289) discloses fluorimetry as a method of measuring the concentration of Ca2+ ions in cells, in which excited light having two wavelengths is used as seen in (e) Optical Measuring Apparatus described on page 281, lines 3-4. Specifically, excited light having two wavelengths is generated by placing a band pass filter of 340 nm and 380 nm on a rotating disk, thereby causing a change in tension forces applied to smooth muscles. Then, the concentration of cell Ca2+ ions is measured using this change. This means that the smooth muscles are relaxed at frequency bands of 340 nm and 380 nm.

Viagra, Cialis, Levitra, or the like have been used as internal medications to increase erectility by inducing relaxation of smooth muscles of a human body. Although these drugs are over-the-counter drugs, many people buy them via illegal distribution channels and are thus likely to misuse or abuse the drugs. If an anginal patient takes such a drug, his/her blood pressure may be sharply lowered and cause a risk, and may have side effects, such as headache, facial blushing, gastroenteric difficulties, nasal congestion, urinary tract infection, deterioration of sight, diarrhea, dizziness, or a skin rash.

As another example of an apparatus for relaxing smooth muscles, there is an apparatus for curing asthma using an electric stimulus, in which the asthma is cured by applying an electric stimulus to a vagus nerve that is directly related to an asthma attack so as to suppress contraction of smooth muscles surrounding the airway. That is, this apparatus is a type of apparatus that relaxes smooth muscles of a human body. This apparatus includes a small electric generator and one electrode. The electric generator is installed outside a human body, and the electrode is inserted into the skin of a side portion of a neck by which the vagus nerve passes. When an electric stimulus is applied using this apparatus, neurons that contract the airway may be deactivated, thus stopping the asthma attack.

However, an apparatus for relaxing smooth muscles, which is capable of increasing the concentration of a material that relaxes smooth muscles of a human body by using light having a predetermined wavelength range of visible light, has yet to be introduced.

SUMMARY OF THE INVENTION

The present invention is directed to an apparatus for relaxing smooth muscles of a human body, which is capable of increasing the concentration of a material that relaxes smooth muscles by directly irradiating light having a predetermined wavelength range, which induces relaxation of smooth muscles of a human body, onto acupuncture points related to an internal organ consisting of smooth muscles via an electrode probe.

The present invention is also directed to an apparatus for relaxing smooth muscles of a human body, which is portable and convenient since an electrode probe is constructed such that the electrode probe is attachable to/detachable from a controller body via a probe connection terminal and may be manipulated at a remote place using a wireless control device.

The present invention is also directed to an apparatus for relaxing smooth muscles of a human body, which is portable, can be used during movement, and is convenient since a wireless electrode probe that can be separated from a controller body is configured as an electrode probe and a plurality of probes can be wirelessly and simultaneously manipulated at a remote place using one controller.

According to an aspect of the present invention, there is provided an apparatus for relaxing smooth muscles of a human body, the apparatus including a controller body configured to determine whether a light irradiation mode is selected and an operation is started through a direct manipulation using a switch, and output a light-emitting diode (LED) driving signal to an electrode probe connection terminal; and a wired electrode probe configured to be attached to/detached from the electrode probe connection terminal to be electrically connected to/disconnected from the controller body, and to be driven by the LED driving signal to emit light having a predetermined wavelength range that increases concentration of a material for relaxing smooth muscles of a human body.

According to another aspect of the present invention, there is provided an apparatus for relaxing smooth muscles of a human body, the apparatus including a wireless control unit configured to wirelessly transmit a remote control signal for selecting a light irradiation mode and starting an operation; a controller body configured to determine whether a light irradiation mode is selected and an operation is started through a direct manipulation using a switch or through a remote manipulation using a wireless control unit, and output an LED driving signal to an electrode probe connection terminal; and a wired electrode probe configured to be attached to/detached from the electrode probe connection terminal to be electrically connected to/disconnected from the controller body, and to be driven by the LED driving signal to emit light having a predetermined wavelength range that increases concentration of a material for relaxing smooth muscles of a human body.

According to another aspect of the present invention, there is provided an apparatus for relaxing smooth muscles of a human body, the apparatus including a wireless control unit configured to wirelessly transmit a remote control signal for selecting a light irradiation mode and starting an operation; a controller body configured to determine whether a light irradiation mode is selected and an operation is started through a direct manipulation using a switch or through a remote manipulation using the wireless control unit, and output an LED driving signal via an electrode probe connection terminal or a wireless transmission unit; a wired electrode probe configured to be attached to/detached from the electrode probe connection terminal to be electrically connected to/disconnected from the controller body, and to be driven by the LED driving signal to emit light having a predetermined wavelength range that increases concentration of a material for relaxing smooth muscles of a human body; and a wireless electrode probe configured to receive the LED driving signal that is wirelessly transmitted and emit light having a predetermined wavelength range that increases concentration of a material for relaxing smooth muscles of a human body.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
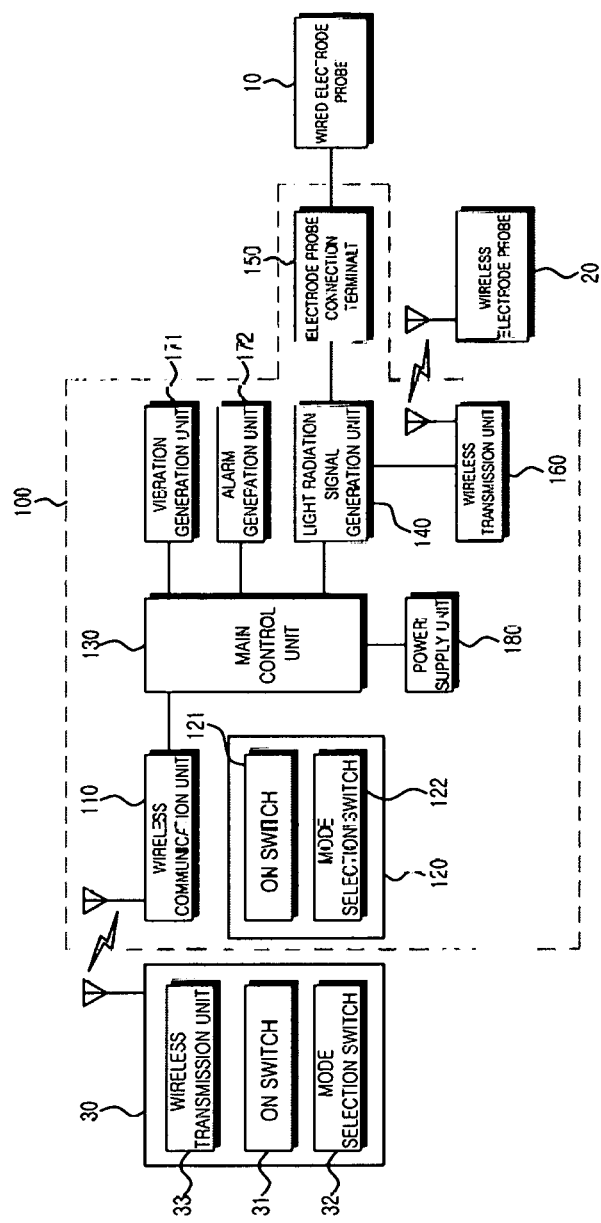
FIG. 1 is a block diagram of an apparatus for relaxing smooth muscles of a human body according to an embodiment of the present invention.

Hereinafter, structures and operations of apparatuses for relaxing smooth muscles of a human body according to various embodiments of the present invention will be described with reference to the accompanying drawings.

The specific terms used in the present specification and claims are not limited to those as defined commonly or as defined in dictionaries and should be interpreted as meanings and concepts that are consistent with the technical idea of the present invention, based on the principle that an inventor can appropriately define the concepts of terms to explain his/her invention in the best way. Thus, the embodiments set forth herein and the structures illustrated in the drawings are merely exemplary embodiments of the present invention. Accordingly, it will be understood by those of ordinary skill in the art that various equivalents and modified examples that may replace these embodiments would have been devised at the filing date of the present invention.

Figure 2:
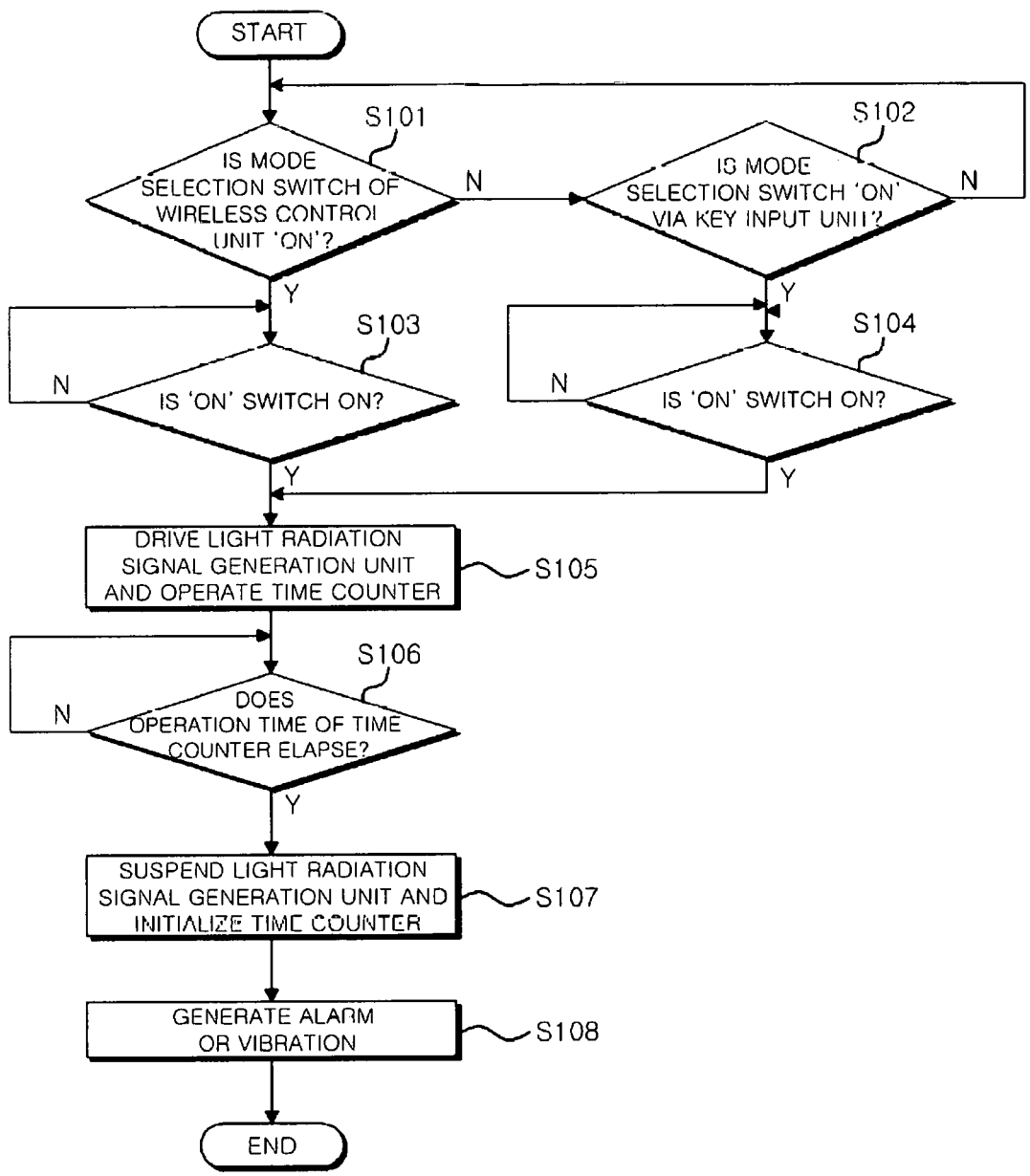
FIG. 2 is a flowchart illustrating a probe driving process performed by a main control unit of an apparatus for relaxing smooth muscles of a human body according to an embodiment of the present invention.
Figure 3:
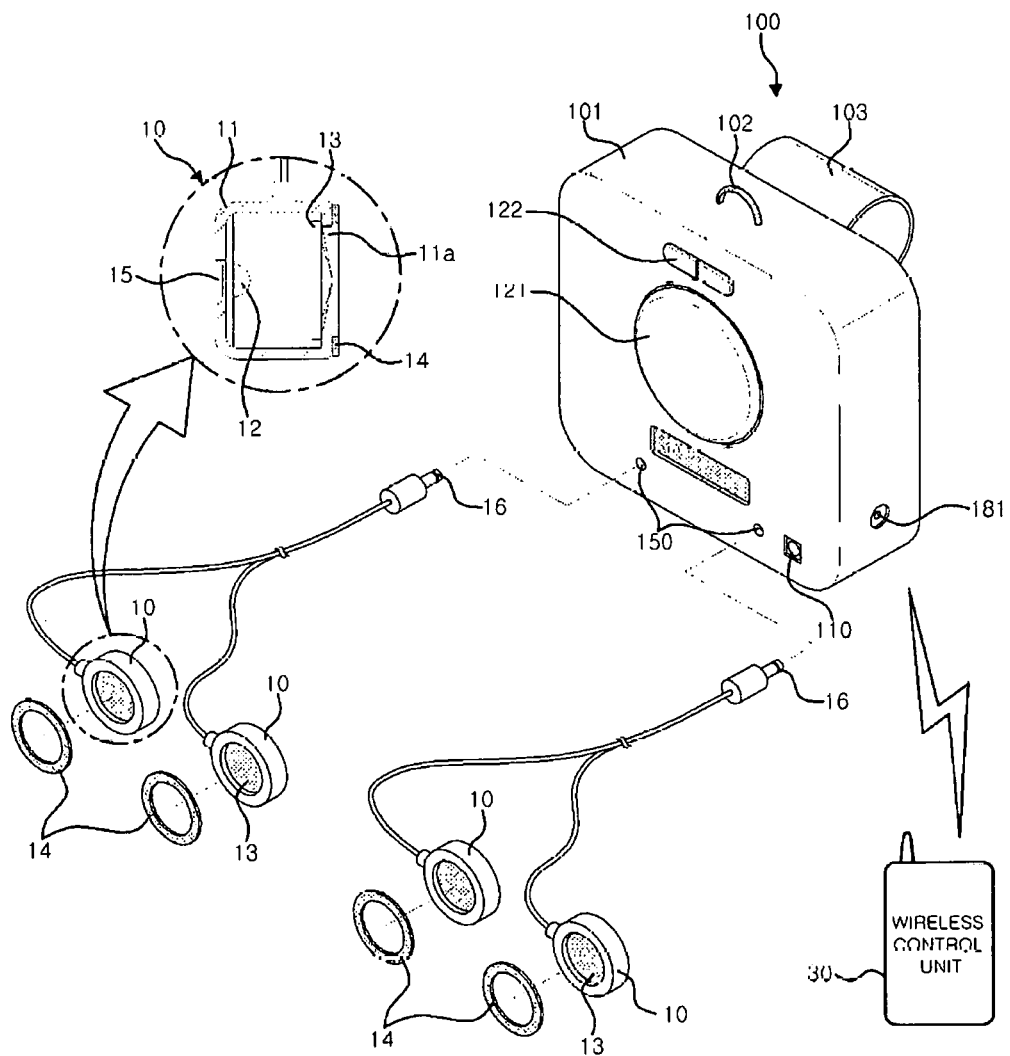
FIG. 3 is a perspective view of an apparatus for relaxing smooth muscles of a human body according to an embodiment of the present invention.
Figure 4:
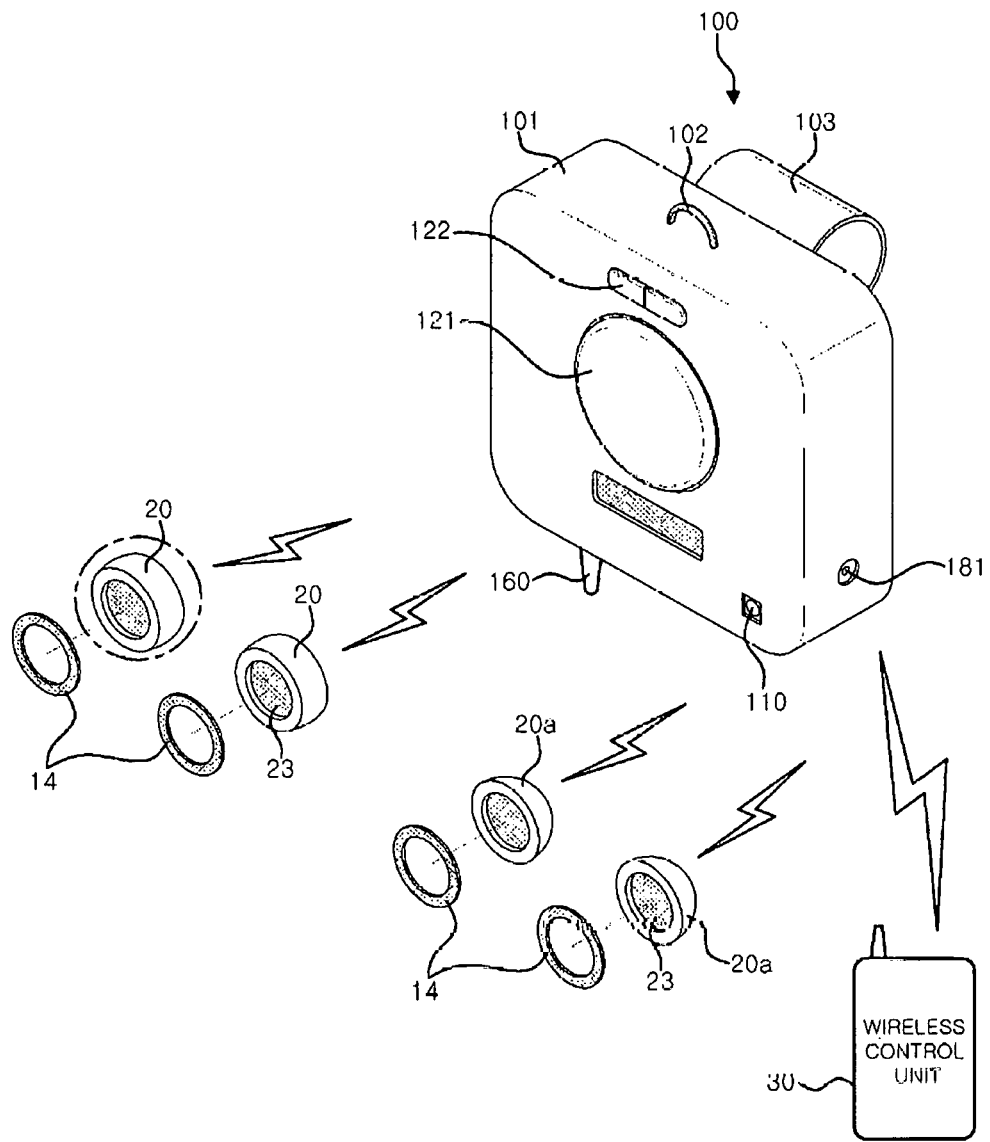
FIG. 4 is a perspective view of an apparatus for relaxing smooth muscles of a human body according to another embodiment of the present invention.
Figure 5A:
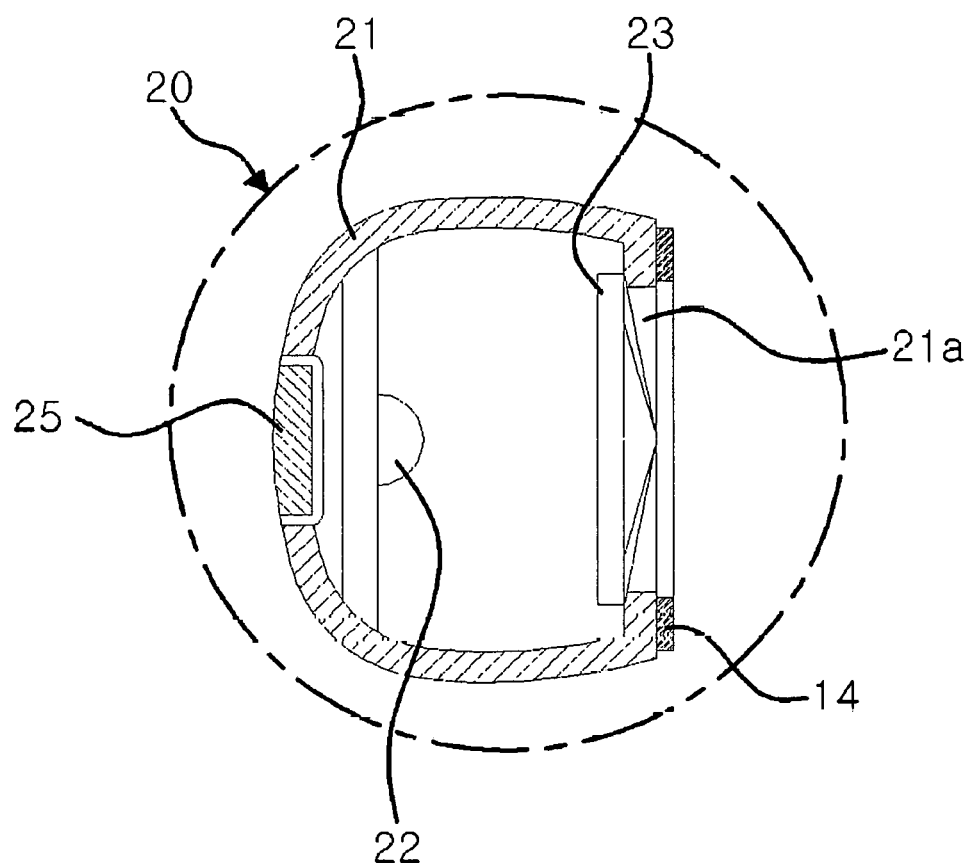
FIGS. 5A and 5B are enlarged cross-sectional views of a wireless electrode probe of FIG. 4 according to embodiments of the present invention.
Figure 5B:
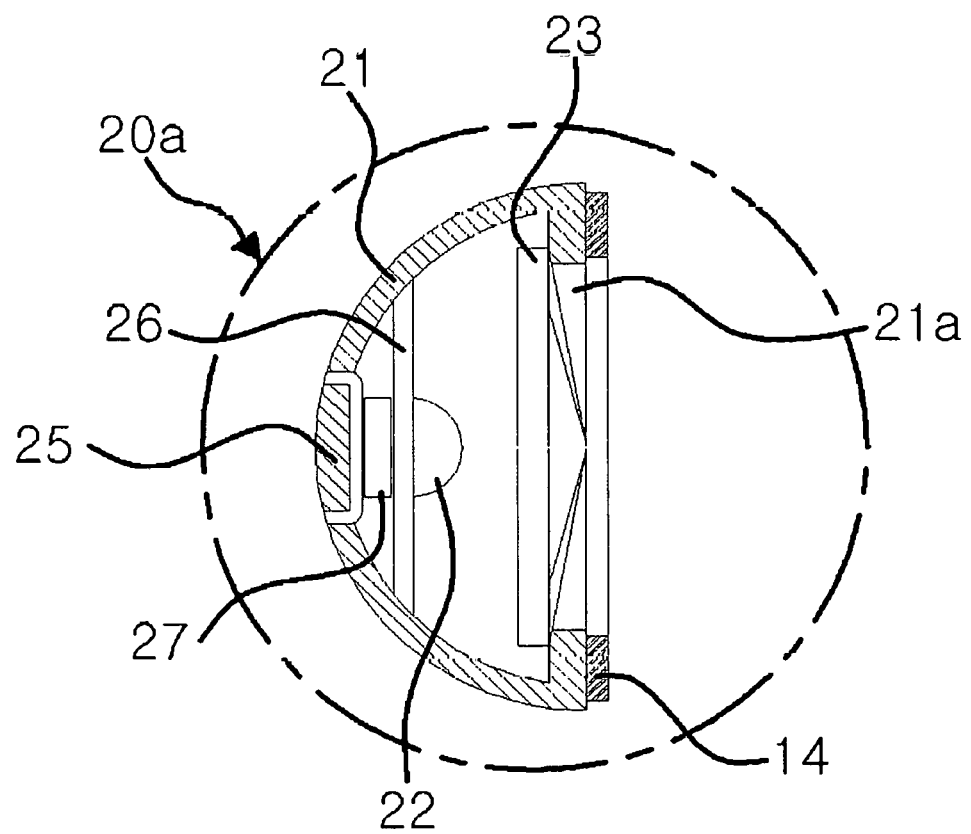

FIG. 1 is a block diagram of an apparatus for relaxing smooth muscles of a human body according to an embodiment of the present invention. FIG. 2 is a flowchart illustrating a probe driving process performed by a main control unit of an apparatus for relaxing smooth muscles of a human body according to an embodiment of the present invention. FIG. 3 is a perspective view of an apparatus for relaxing smooth muscles of a human body according to an embodiment of the present invention. FIG. 4 is a perspective view of an apparatus for relaxing smooth muscles of a human body according to another embodiment of the present invention. FIGS. 5A and 5B are enlarged cross-sectional views of a wireless electrode probe of FIG. 4 according to embodiments of the present invention.

According to an embodiment of the present invention, the apparatus may include a wired electrode probe 10 and a controller body 100. According to another embodiment of the present invention, the apparatus may further include a wireless control unit 30, and/or wireless electrode probes 20 and 20a. However, according to an exemplary embodiment of the present invention, the apparatus may include the wired electrode probe 10, the wireless electrode probes 20 and 20a, the wireless control unit 30, and the controller body 100 as illustrated in FIG. 1. In this case, the controller body 100 includes a wireless communication unit 110, an operation selection unit 120, a main control unit 130, a light irradiation signal generation unit 140, an electrode probe connection terminal 150, a wireless transmission unit 160, and a power supply unit 180. Optionally, the controller body 100 may further include a vibration generation unit 171 and/or an alarm generation unit 172. Hereinafter, the structure and operations of an apparatus for relaxing smooth muscles of a human body according to the present invention will be described based on the exemplary embodiment.

The wired electrode probe 10 may be attached to/detached from the electrode probe connection terminal 150 of the controller body 100 to be electrically connected to/disconnected from the controller body 100. Thereby, the wired electrode probe 10 may be driven by a light-emitting diode (LED) driving signal, which is output from the controller body 100, to emit light having a predetermined wavelength range that increases the concentration of a material for relaxing smooth muscles of a human body. The wired electrode probe 10 includes an electrode case 11, an LED 12, an optical filter 13, and a double-faced adhesive sticker 14, as illustrated in the enlarged view of FIG. 3, marked by dotted lines.

The wireless electrode probes 20 and 20a are installed separately from the controller body 100. The wireless electrode probes 20 and 20a each include a wireless receiving unit to establish wireless communication with the wireless transmission unit 160 of the controller body 100. Via the wireless receiving unit, each of the wireless electrode probes 20 and 20a wirelessly receives the LED driving signal from the controller body 100, and is driven by the LED driving signal to emit light having a predetermined wavelength range that increases the concentration of a material for relaxing smooth muscles of a human body. Each of the wireless electrode probes 20 and 20a includes an electrode case 21 having an internal space; an LED 22, an optical filter 23, a wireless receiving circuit and battery 27, a printed circuit board (PCB) 26 including a charging circuit for charging the wireless receiving circuit and battery 27 and an 'on/off' switch circuit, which are accommodated in the electrode case 21; and a double-faced adhesive sticker 14 adhered to openings of the electrode case 21, as illustrated in the enlarged views of FIGS. 5A and 5B. The LED 22 is installed on the PCB 26 on which the charging circuit and the 'on/off' switch circuit are mounted. When a plurality of wireless electrode probes 20 and 20a are used, the plurality of wireless electrode probes 20 and 20a are configured such that operations thereof are simultaneously started and ended according to one LED driving signal transmitted via the wireless transmission unit 160 of the controller body 100.

Figures 8A, 8B:
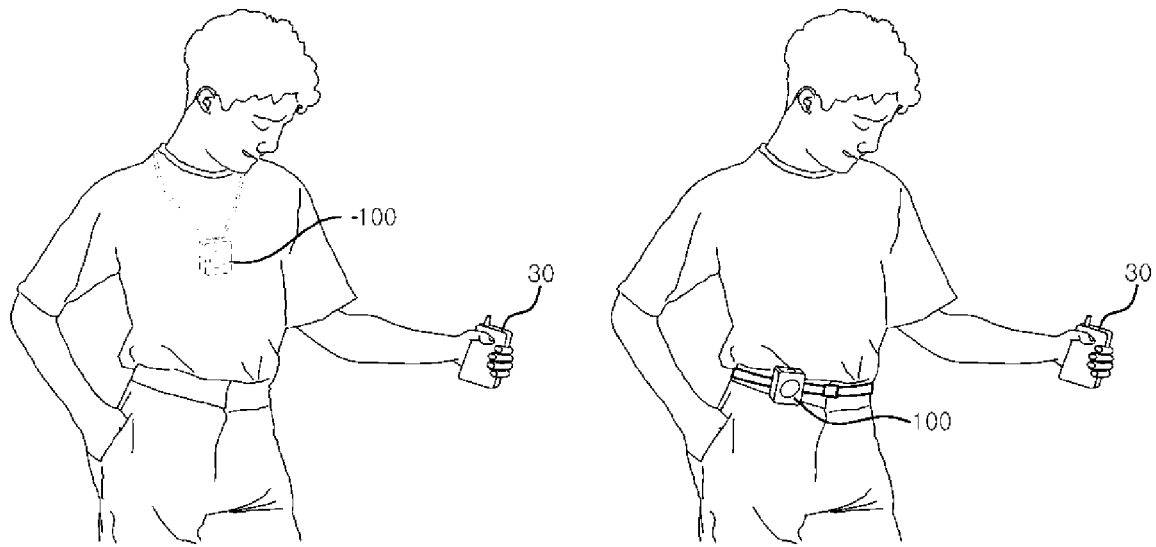
FIGS. 8A and 8B are reference diagrams illustrating states in which a user caries an apparatus for relaxing smooth muscles of a human body using a ring or clip.

The wireless control unit 30 includes an 'on' switch 31 configured to start an operation, a mode selection switch 32 configured to select a mono-color light irradiation mode or a sequential multi-color light irradiation mode, and a wireless transmission unit 33 configured to establish wireless communication. The wireless control unit 30 wirelessly transmits a light irradiation mode selection signal and an operation starting signal when the 'on' switch 31 and the mode selection switch 32 are 'on,' respectively. The wireless control unit 30 may be configured to establish wireless communication with the wireless communication unit 110 according to one of a radio-frequency (RF) mode, a Bluetooth mode, and a ZigBee mode. To this end, a program for transmitting the light irradiation mode selection signal may be installed in the wireless control unit 30 or the wireless control unit 30 may be embodied as a portable wireless communication terminal that provides a user interface (UI) screen, e.g., a personal computer (PC), a notebook computer, a smart phone, or a personal digital assistant (PDA). The program and the UI screen would be apparent to those of ordinary skill in the art and may be embodied in any of various forms. For example, if a user selects the mono-color light irradiation mode or the sequential multi-color light irradiation mode using a smooth muscle relaxing icon contained in either a background image installed in a PC or a notebook computer or a widget image installed in a smart phone or a PDA, then the program and the UI screen may be configured to transmit the light irradiation mode selection signal and the operation starting signal to the outside. Also, the wireless control unit 30 may be configured such that a user can carry it with his/her hand (see FIGS. 8A and 8B).

The controller body 100 includes the wireless communication unit 110, the operation selection unit 120, the main control unit 130, the light irradiation signal generation unit 140, the electrode probe connection terminal 150, the wireless transmission unit 160, and the power supply unit 180. The controller body 100 determines whether a light irradiation mode is selected and an operation is started through a direct manipulation using the mode selection switch 122 of the operation selection unit 120 or through a remote manipulation using the wireless control unit 30, and then either outputs an LED driving signal to the electrode probe connection terminal 150 so as to operate at least one wired electrode probe 10 or wirelessly transmits the LED driving signal via the wireless transmission unit 160 so as to operate at least one of the wireless electrode probes 20 and 20a based on a result of the determination. As illustrated in FIGS. 3 and 4, the controller body 100 may be mounted in one main body housing 101, and a ring 102 or a clip 103 may be formed at a side of or the rear of the main body housing 101 such that a user may wear the main body housing 101 with a string or a belt.

The wireless communication unit 110 wirelessly receives the light irradiation mode selection signal and the operation starting signal from the wireless transmission unit 33 of the wireless control unit 30, and delivers them to the main control unit 130.

The operation selection unit 120 includes an 'on' switch 121 configured to start an operation, and a mode selection switch 122 configured to select a mono-color light irradiation mode or a sequential multi-color light irradiation mode. The operation selection unit 120 transmits the light irradiation mode selection signal and the operation starting signal to the main control unit 130 when the 'on' switch 121 and the mode selection switch 122 are 'on', respectively.

The main control unit 130 outputs a light irradiation control signal for controlling an operation of the light irradiation signal generation unit 140 according to whether the light irradiation mode selection signal and the operation starting signal are input through a switch input via the operation selection unit 120 or through a remote manipulation using the wireless control unit 30. Whenever the operation starting signal is input, the main control unit 130 outputs the light irradiation control signal for a predetermined time period, e.g., for thirty minutes, and blocks the output of the light irradiation control signal after the predetermined time period. To this end, a process of a control logic illustrated in the flowchart of FIG. 2 is installed in the main control unit 130. The process includes determining whether the light irradiation mode selection signal and the operation starting signal are input through a remote manipulation using the wireless control unit 30 or through a direct manipulation using the operation selection unit (operations S101 to S104), outputting the light irradiation control signal for controlling driving of the light irradiation signal generation unit 140 and operating a time counter (not shown) when it is determined that the light irradiation mode selection signal and the operation starting signal are input (operation S105), checking whether an operating time of the time counter elapses, and outputting the light irradiation control signal for suspending the operation of the light irradiation signal generation unit 140 and initializing the time counter when it is determined that an operating time of the time counter elapses (operations S106 and S107), and generating an alarm or vibration indicating the end of the operation of the light irradiation signal generation unit 140 (operation S108).

The light irradiation signal generation unit 140 is controlled by the light irradiation control signal output from the main control unit 130 to output the LED driving signal for outputting mono-color light or sequentially outputting multi-color light.

The electrode probe connection terminal 150 includes at least one electrode terminal to or from which an electrode pin 16 of the wired electrode probe 10 may be electrically connected or disconnected. As illustrated in FIG. 3, each of the at least one electrode terminal may be exposed outside the main body housing 101 of the controller body 100 such that the electrode pin 16 of the wired electrode probe 10 may be inserted into each of the at least one electrode terminal.

The wireless transmission unit 160 transforms the LED driving signal received from the light irradiation signal generation unit 140 into a radio signal, and wirelessly transmits the radio signal via an antenna (not shown), according to the selected light irradiation mode.

The vibration generation unit 171 and the alarm generation unit 172 are driven by the main control unit 130 to generate a vibration and an alarm, respectively, at a point of time when the output of the light irradiation control signal is blocked.

The power supply unit 180 supplies driving power to the elements of the wired electrode probe 10 and the controller body 100, and may include a charging battery. When power of the charging battery is completely consumed, a charging adapter may be inserted into the power supply unit 180 via a charging jack 181 to supply power. The charging adapter may generate a constant voltage, and preferably, 12 V or 5 V when it is connected to a general alternating current (AC) power supply terminal. The charging adapter would be apparent to those of ordinary skill in the art although the charging adapter is not illustrated and described in detail.

The electrode case 11 of the wired electrode probe 10 and the electrode cases 21 of the wireless electrode probes 20 and 20a are hollow electrode cases each having a cylindrical shape, a jar shape, or a hemispheric shape as illustrated in FIGS. 3 to 5B. The electrode cases 11 and 21 are configured such that front parts thereof are open to form openings 11a and 21a and internal spaces are formed to accommodate the LEDs 12 and 22 and the optical filters 13 and 23, respectively. Although each of the electrode cases 11 and 21 is illustrated as having the cylindrical shape, the jar shape, or the hemispheric shape, the present invention is not limited thereto and each of the electrode cases 11 and 21 may have any of other various shapes, e.g., a flat cylindrical shape, an oval shape, or a heart shape.

The LEDs 12 and 22 are installed within the electrode cases 11 and 21 such as to emit light toward the openings 11a and 21a of the electrode cases 11 and 21, respectively, and may thus emit visible light having a predetermined wavelength range for inducing relaxation of smooth muscles of a human body. The LEDs 12 and 22 emit colored light (e.g., orange, red, green, or yellow light) having a predetermined wavelength range, e.g., 400 nm to 800 nm, and may each be embodied as a mono-color LED, a three-color LED, an organic LED, or the like. For example, when the light irradiation signal generation unit 140 outputs an LED driving signal for emitting mono-color light, the LED 12 emits mono-color light, e.g., orange, red, green, or yellow light. In this case, when a plurality of wired electrode probes 10 are connected to at least one electrode probe connection terminal 150, the plurality of wired electrode probes 10 may emit mono-color light of the same color or may each emit mono-color light of a different color. In contrast, when the light irradiation signal generation unit 140 outputs an LED driving signal for sequentially emitting multi-colored light, the LED 12 of the wired electrode probe 10 emits multi-color light having four colors, e.g., orange, red, green, and yellow light, or multi-color light having two colors according to a predetermined order. For example, either orange light, red light, green light, and yellow light or orange light and red light may be sequentially emitted. When the light irradiation signal generation unit 140 outputs an LED driving signal for emitting mono-color light at a predetermined frequency, the LED 12 of the wired electrode probe 10 emits the mono-color light at the predetermined frequency. Similarly, a plurality of wireless electrode probes 20 and 20a emit light.

The optical filters 13 and 23 are installed in the openings 11a and 21a of the electrode cases 11 and 21 to be spaced a predetermined distance from the LEDs 12 and 22, so that visible light emitted from the LEDs 12 and 22 may pass through the optical filters 13 and 23 to be filtered and focused. In particular, each of the optical filters 13 and 23 may be formed of a material selected from quartz, crystal, and crystal glass, and may have a transparent surface that is cut to have a polygonal shape, e.g., a pentagonal, hexagonal, or octagonal shape, or to have a convex lens shape, so that visible light emitted from the LEDs 12 and 22 may be concentrated and irradiated onto acupuncture points related to an internal organ consisting of smooth muscles of a human body via the openings 11a and 21a of the electrode cases 11 and 21.

The double-faced adhesive sticker 14 includes an adhesive layer on both surfaces thereof, so that one of the surfaces may be adhered onto peripheral portions of the openings 11a and 21a of the electrode cases 11 and 21 and the openings 11a and 21a may be attached to a human body via the other surface.

The wired electrode probe 10 further includes a terminal switch 15 and each of the wireless electrode probes 20 and 20a further includes a terminal switch 25 to turn on/off light emission operations of the electrode probes 10, 20a and 20b according to an LED driving signal transmitted from the controller body 100 in a wired or wireless manner.

Overall operations and effects of an apparatus for relaxing smooth muscles of a human body using light energy according to an embodiment of the present invention will now be described.

First, a method of increasing the erectility of, for example, a cavernous body consisting of smooth muscles will be described to learn the principle of relaxing smooth muscles of a human body. In general, a key principle to increasing erectility is to relax the smooth muscles of the cavernous body to a maximum level so that the cavernous body may absorb a sufficient amount of blood. It has been known that relaxation of the smooth muscles of a cavernous body is closely related to an increase in the concentration of cyclic adenosine monophosphate (cAMP) or cyclic guanylate monophosphate (cGMP) in cells. Viagra, which has been placed on the market, is based on this principle.

Accordingly, the present invention is based on the fact that the concentration of cAMP and a rate of deoxyribonucleic acid (DNA)/ribonucleic acid (RNA) synthesis increase when visible light having a predetermined wavelength range of 400 nm to 800 nm is irradiated onto mammalian cells for a predetermined time (T.I. KARU, Biological action of low-intensity visible monochromatic light and some of its medical application, International Congress on laser in medicine and surgery, Bologna, Jun. 26, 1985; T.I. KARU, O.A. TIPHLOVA, Effect of irradiation with monochromatic visible light on cAMP content in Chinese hamster fibroblasts, IL NUOVO CIMENTO, vol. 9D, N. 10, pp. 1245-1250, 1987); the fact that when light is irradiated onto acupuncture points, the light is delivered to acupuncture points or organs connected to meridians via the meridians (Sergei Pankratov, Meridian conducts light, Raum & Zeit, Germany, 1991); and the fact that acupuncture points are connected to internal organs via meridians, and qihai (CV6), which refers to a sea at which energies of a body are collected, guanyuan (CV4) at which vital forces of a body are collected, and zhongji (CV3) that is an acupuncture point related to genitourinary organs are main acupuncture points related to sex functions as seen in oriental medical books Dongui Bogam and Huangdi Neijing.

Based on these facts, according to the present invention, the wired electrode probe 10 or the wireless electrode probes 20 and 20a configured to emit visible light having a wavelength of 400 nm to 800 nm are directly attached to acupuncture points 40, i.e., the qihai (CV6), the guanyuan (CV4), the zhongji (CV3), and the like, which are related to sex functions of a human body, and light energy is irradiated onto the acupuncture points 40 for a predetermined time period, e.g. for thirty minutes, every day. Then, the light irradiated onto the acupuncture points 40 supplies light energy to tissue cells related to erectility via meridians, and is then delivered to cells of smooth muscles of a cavernous body to induce relaxation of the smooth muscles of the cavernous body, thereby causing smooth blood circulation and increasing erectility.

Figure 6:
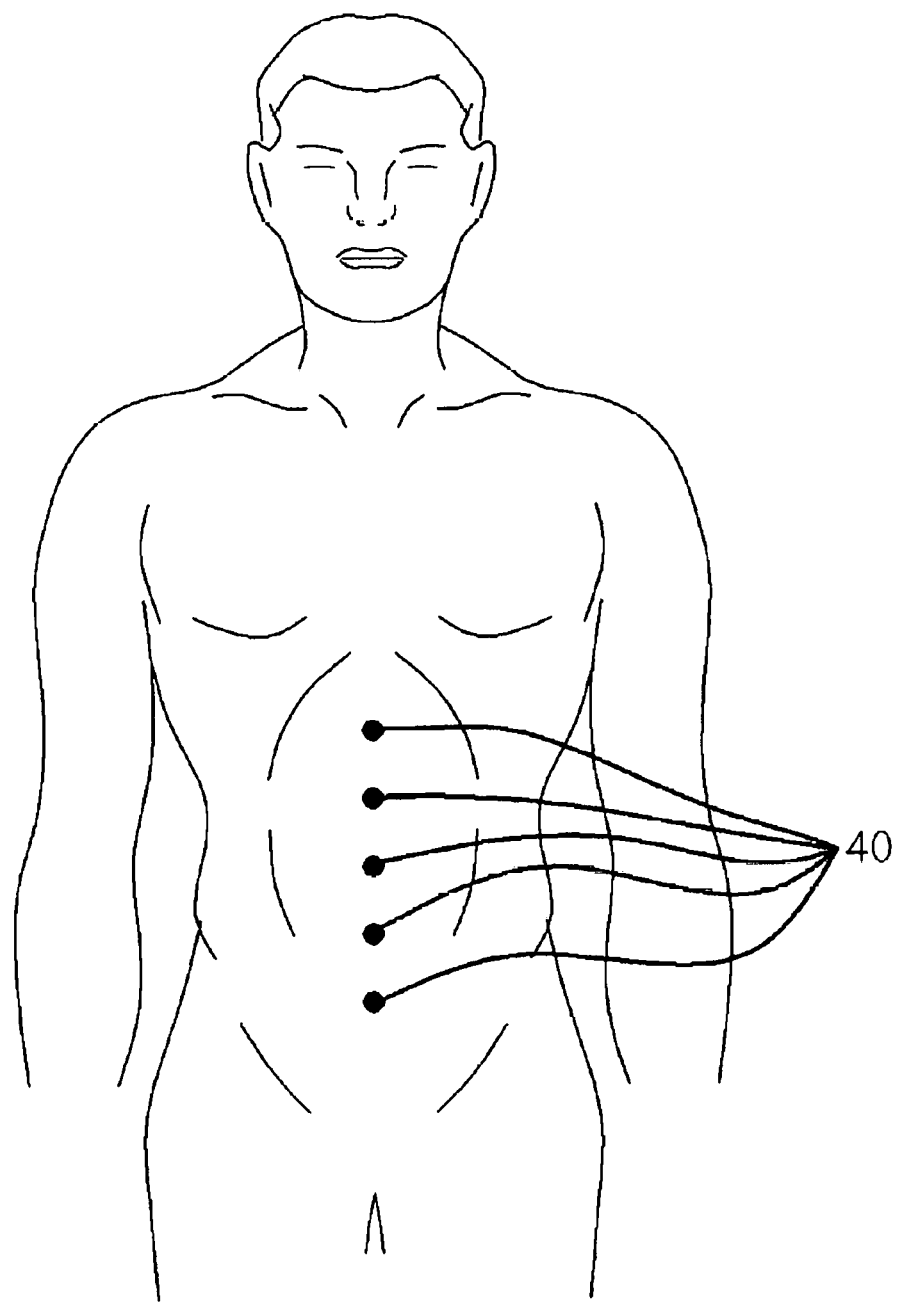
FIG. 6 is a reference diagram illustrating locations of acupuncture points related to an internal organ consisting of smooth muscles.
Figure 7A:
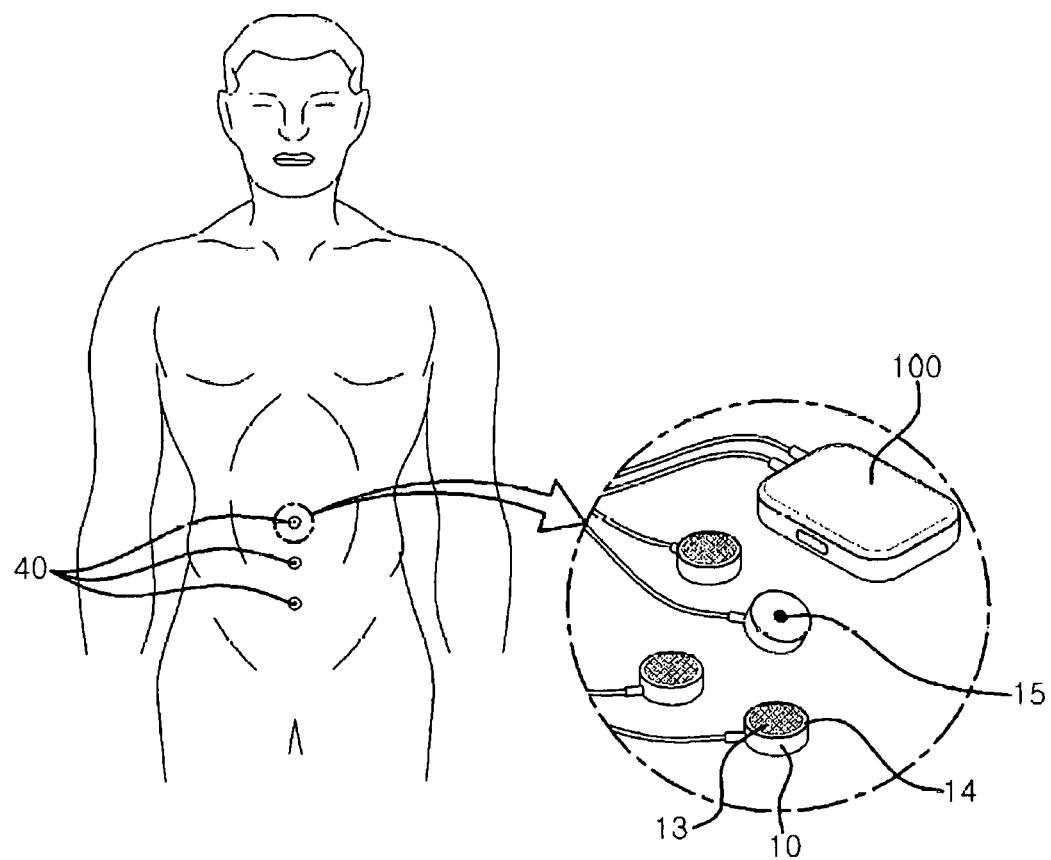
FIGS. 7A and 7B are reference diagrams illustrating states in which an apparatus for relaxing smooth muscles of a human body is attached to acupuncture points related to an internal organ consisting of smooth muscles.
Figure 7B:
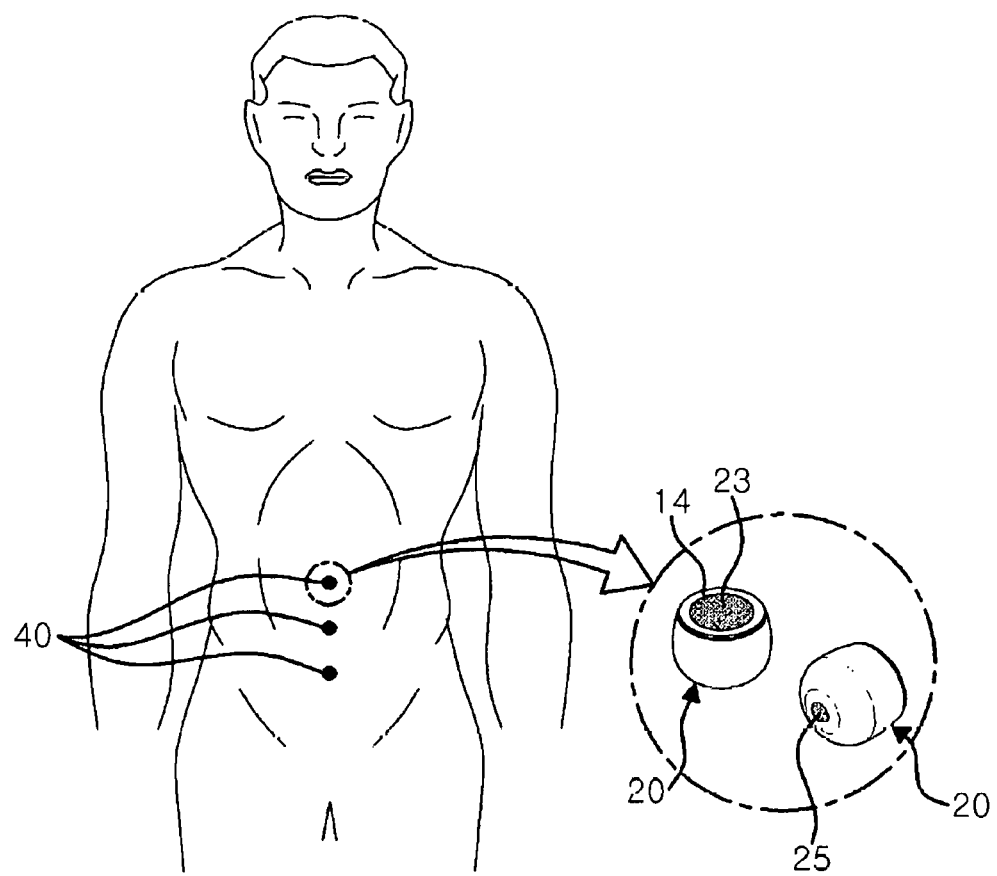

FIG. 6 is a reference diagram illustrating locations of acupuncture points 40 related to sex functions: the qihai (CV6), which refers to a sea at which energies of a body are collected, the guanyuan (CV4) at which vital forces of a body are collected, and the zhongji (CV3) related to genitourinary organs FIGS. 7A and 7B are reference diagrams illustrating states in which an apparatus for relaxing smooth muscles of a human body is attached to the acupuncture points 40 of FIG. 6. FIGS. 8(*a*) and (*b*) are reference diagrams illustrating states in which a user carries an apparatus for relaxing smooth muscles of a human body by using a ring or clip.

A method of using the apparatus will now be described. In order to use a wired electrode probe, first, a user inserts the electrode pin 16 connected to at least one wired electrode probe 10 into the electrode probe connection terminal 150 of the controller body 100. When the wireless electrode probes 20 and 20a are used, this process is omitted.

Then, the user adheres one surface of the double-faced adhesive sticker 14 to a peripheral part of the opening 11a of the electrode case 11 of the wired electrode probe 10 (or the electrode case 21 of the wireless electrode probes 20 and 20a), and adheres the other surface of the double-faced adhesive sticker 14 to the acupuncture points.

While the apparatus is attached to the acupuncture points, when the mono-color light irradiation mode or the sequential multi-color irradiation mode is selected by manipulating either the mode selection switch 122 of the operation selection unit 120 or the mode selection switch 32 of the wireless control unit 30, a light irradiation mode selection signal indicating the selected mode may be output from the operation selection unit 120 or the wireless transmission unit 33 of the wireless control unit 30.

The output light irradiation mode selection signal is directly input to the main control unit 130 of the controller body 100 or is input to the main control unit 130 via the wireless communication unit 110. Then, whenever the user turns on the 'on' switch 121 of the controller body 100 or the 'on' switch 31 of the wireless control unit 30, an operation starting signal may be output from the operation selection unit 120 or the wireless control unit 30 and then be input to the main control unit 130

Thus, whenever the operation starting signal is input to the main control unit 130, the main control unit 130 operates a time counter (not shown), outputs a light irradiation control signal, and transmits the light irradiation control signal to the light irradiation signal generation unit 140 while checking whether an operating time of the time counter elapses. Then, in order to increase erectility, the light irradiation signal generation unit 140 turns on the LED 12 of the wired electrode probe 10 via the electrode probe connection terminal 150 or the LEDs 22 of the wireless electrode probes 20 and 20a via the wireless transmission unit 160 by outputting an LED driving signal for emitting mono-color light, e.g., orange, red, green, or yellow light, which has a predetermined wavelength range of, for example, 400 nm to 800 nm. Thus, colored light emitted from the LEDs 12 of a plurality of wired electrode probes 10 (or the LEDs 22 of a plurality of wireless electrode probes 20 and 20a) is filtered and focused by a plurality of optical filters 13 (or 23) and then concentrated and irradiated onto acupuncture points related to sex functions via the openings 11a of the electrode cases 11 (openings 21a of the electrode cases 21). During the irradiation of the colored light, the terminal switches 15 of the plurality of wired electrode probes 10 (or of the terminal switches 25 of the plurality of wireless electrode probes 20 and 20a) may be turned on/off to individually control the light irradiation operations of the plurality of electrode probes 10 (or 20 and 20a).

As described above, after the operation starting signal is output from the main control unit 130, the main control unit 130 determines whether a predetermined time period, for example, thirty minutes, elapses using the time counter, and initializes the time counter and outputs an LED driving stopping signal to suspend the light irradiation when it is determined that the predetermined time elapses. In this case, the alarm generation unit 172 generates an alarm sound or voice and the vibration generation unit 171 generates a vibration so that a user may be informed of the suspension of the light irradiation. When the LED driving stopping signal is input to the light irradiation signal generation unit 140, the light irradiation signal generation unit 140 stops an output of an LED driving signal. In this case, outputs of the LEDs 12 of the plurality of wired electrode probes 10 (or of the LEDs 22 of the plurality of wireless probe electrodes 20 and 20a) are stopped, and the LEDs 12 (or the LEDs 22) are turned off.

In this case, when the user desires to continue light irradiation using colored light, the user may press the 'on' switch 31 of the wireless control unit 30 or the 'on' switch 121 of the controller body 100 once again so as to start the light irradiation. Whenever the user presses the 'on' switch 31 or 121 once, the light irradiation using colored light is performed.

An apparatus for relaxing smooth muscles of a human body according to the present invention as described above is not limited to the embodiments set forth herein, and may also be applied to the fields of disease treatment and prevention of all organs consisting of smooth muscles of a human body, e.g., treatment of menstrual cramps, sterility, high blood pressure, tension headaches, migraines, lymphedema, and underlying edema, promotion of exercise of blood vessels and lymphatic vessels, urinary incontinence treatment, prostate treatment, promotion of exercise of large and small intestines, and treatment of reflux esophagitis. It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

INDUSTRIAL APPLICABILITY

The present invention relates to an apparatus for relaxing smooth muscles of a human body, which is capable of inducing relaxation of smooth muscles of a human body using an electrode probe that irradiates light having a predetermined wavelength range, and is applicable to the fields of disease treatment and prevention of all organs consisting of smooth muscles of a human body, e.g., treatment of menstrual cramps, sterility, high blood pressure, tension headaches, migraines, lymphedema, and underlying edema, promotion of exercise of blood vessels and lymphatic vessels, urinary incontinence treatment, prostate treatment, promotion of exercise of large and small intestines, and treatment of reflux esophagitis.

What is claimed is:

1. An apparatus for relaxing smooth muscles of a human body, comprising:
   a controller body configured to determine whether a light irradiation mode is selected and an operation is started through a user's manipulation, the controller body comprising a wireless transmission unit configured to transform an LED driving signal output according to the selected light irradiation mode into a radio signal and transmit the radio signal; and
   a wireless electrode probe configured to wirelessly receive the LED driving signal from the controller body by establishing wireless communication with the wireless transmission unit, the wireless electrode probe comprising an LED configured to emit light,
   wherein the LED is configured to be driven by the LED driving signal received from the controller body to emit the light of a predetermined wavelength range, which increases concentration of a material for relaxing smooth muscles of a human body.

2. The apparatus of claim 1, wherein the controller body comprises:
   an operation selection unit including at least one switch for selecting a light irradiation mode and starting an operation, and configured to deliver a light irradiation mode selection signal and an operation starting signal to a main control unit according to an input of the at least one switch;
   the main control unit configured to output a light irradiation control signal for controlling an operation of a light irradiation signal generation unit, according to whether the light irradiation mode selection signal and the operation starting signal are input through an input of the at least one switch; and
   the light irradiation signal generation unit configured to generate the LED driving signal under control of the light irradiation control signal output from the main control unit.

3. The apparatus of claim 2, wherein the main control unit outputs the light irradiation control signal for a predetermined time period according to whether the operation starting signal is input, and blocks the output of the light irradiation control signal after the predetermined time period.

4. The apparatus of claim 2, wherein the controller body comprises at least one of:
   a vibration generation unit configured to be driven by the main control unit to generate vibration at a point of time when the output of the light irradiation control signal is blocked; and
   an alarm generation unit configured to be driven by the main control unit to generate alarm at the point of time when the output of the light irradiation control signal is blocked.

5. The apparatus of claim 1, further comprising a wireless control unit configured to establish wireless communication with at least one switch of the controller body for selecting a light irradiation mode and starting an operation, and configured to wirelessly transmit a light irradiation mode selection signal and an operation starting signal according to an input of the at least one switch,
   wherein the controller body further comprises a wireless communication unit configured to wirelessly receive the light irradiation mode selection signal and the operation starting signal from the wireless control unit and transmit the light irradiation mode selection signal and the operation starting signal to a main control unit.

6. The apparatus of claim 5, wherein the wireless control unit is configured to establish wireless communication with the wireless communication unit according to one of a radio-frequency (RF) mode, a Bluetooth mode, and a ZigBee mode.

7. The apparatus of claim 1, wherein the wireless electrode probe comprises:
   an electrode case configured to have a front opening and an internal space and
   an optical filter,
   wherein the LED is accommodated in the electrode case and configured to emit light toward the front opening of the electrode case and
   wherein the optical filter is installed in the front opening of the electrode case to be spaced a predetermined distance apart from the LED and configured to allow the light emitted from the LED to pass therethrough so that the light is filtered and focused.

8. The apparatus of claim 7, wherein the wireless electrode probe further comprises;
   a double-faced adhesive sticker including an adhesive layer on both surfaces thereof, and wherein one of the surfaces is adhered onto a peripheral portion of the front opening of the electrode case and the front opening of the electrode case is configured to be attached to a human body via the other surface of the double-faced adhesive sticker.

9. The apparatus of claim 7, wherein the optical filter is formed of one selected from quartz, crystal, and crystal glass, and comprises a transparent surface that is cut to have a polygonal shape or a convex lens shape such that visible light emitted from the LED is concentrated and irradiated onto acupuncture points related to an organ including smooth muscles via the front opening of the electrode case.

10. The apparatus of claim 1, wherein the wireless electrode probe further comprises a terminal switch configured to turn on or off a light emission operation of the wireless electrode probe according to the LED driving signal that is transmitted from the controller body in a wireless manner.

11. The apparatus of claim 1, wherein the wireless electrode probe comprises a plurality of electrode probes, operations of which are simultaneously started and ended according to an LED driving signal transmitted from the wireless transmission unit of the controller body.

12. The apparatus of claim 1, wherein the controller body is mounted in a main body housing,
wherein a ring or a clip is formed at one side of or a rear of the main body housing such that the apparatus is wearable using a string or a belt.

* * * * *